United States Patent [19]

Bertolini

[11] Patent Number: 5,270,054

[45] Date of Patent: Dec. 14, 1993

[54] COSMETIC CAPSULES

[75] Inventor: Peter Bertolini, Huntington, Conn.

[73] Assignee: Chesebrough-Pond's USA Co., Division of Conopco, Inc., Greenwich, Conn.

[21] Appl. No.: 940,104

[22] Filed: Sep. 3, 1992

[51] Int. Cl.$^5$ .............................................. A61K 9/48
[52] U.S. Cl. .................................. 424/451; 206/528; 206/530; 206/531; 206/532; 424/401; 424/453; 424/456; 514/953; 514/962
[58] Field of Search .............. 206/528, 530, 531, 532, 206/601; 424/401, 451, 453, 456; 514/953, 962

[56] References Cited

U.S. PATENT DOCUMENTS

| D. 314,441 | 2/1991 | Hausen | D24/104 |
|---|---|---|---|
| 587,327 | 8/1897 | Planten | 206/528 |
| 2,134,489 | 10/1938 | Scherer | 222/107 |
| 2,334,600 | 11/1943 | Boysen | 222/107 |
| 2,397,051 | 3/1946 | Scherer | 206/530 X |
| 2,525,958 | 10/1950 | Seager et al. | 206/530 |
| 2,562,402 | 7/1951 | Winsten | 206/530 X |
| 2,580,414 | 1/1952 | Duffey | 424/408 |
| 2,718,980 | 9/1955 | Strom | 220/306 |
| 2,797,805 | 7/1957 | Berard | 206/530 X |
| 3,993,223 | 11/1976 | Welker, III et al. | 206/528 X |
| 4,787,536 | 11/1988 | Widerstrom | 206/532 X |
| 4,871,091 | 10/1989 | Priziosi | 206/532 X |
| 5,063,057 | 11/1991 | Spellman et al. | 424/401 |

FOREIGN PATENT DOCUMENTS 63-107906  7/1988  Japan .
520438  4/1940  United Kingdom .

OTHER PUBLICATIONS

R. P. Scherer Brochure entitled "Standard shapes and sizes of the softgel dosage form".

Primary Examiner—Thurman K. Page
Assistant Examiner—Robert H. Harrison
Attorney, Agent, or Firm—Milton L. Honig

[57]  ABSTRACT

A cosmetic product is provided that stores a cosmetic composition in a capsule having a spheroidal body with hollow chamber forming a major portion of the capsule, a tab forming a minor portion of the capsule, and a neck section connecting the tab with the spheroidal body. At least two wings are positioned along opposite sides of the spheroidal body perpendicularly extending outward therefrom. Upon twisting, the neck can be broken to allow release of cosmetic composition from within the chamber.

13 Claims, 1 Drawing Sheet

COSMETIC CAPSULES

BACKGROUND OF THE INVENTION

1. Field of the Invention

The invention concerns capsules containing unit doses of cosmetic compositions.

2. The Related Art

Cosmetics are generally packaged in relatively large containers in amounts that provide multiple doses. Bulk packaging has certain disadvantages. Once opened, the contents of a package become exposed to moisture and air. These forces can be quite detrimental to sensitive ingredients forming the cosmetic product. With bulk packaging, a manufacturer also cannot control individual dosage levels which are most effective and safe; the consumer is burdened with this responsibility. Invariably, usage will either be too high or too low.

Single or unit dose packages of various descriptions have been disclosed in the art. Capsules are one of the newest vehicles for delivering unit dosages of cosmetic products. Recently the Revlon Corporation introduced a product called Age-less ®. The product is a composition of vitamin E, sunscreens and moisturizers which have been sealed into vitamin-like capsules. These elongated capsules are meant to be pierced and their contents squeezed onto the skin. Certain problems are, however, associated with the packaging vehicle. For instance, a sharp pointed instrument is necessary to pierce the capsule walls; this may readily lead to injury An opening mechanism that would avoid necessity for procuring any opening instrument would also be more convenient. Furthermore, there is danger in shaping cosmetic products to look like vitamins. Children, or even adults, may inadvertently mistake the product and ingest it.

La Prairie Corporation has marketed a cosmetic called Skin Caviar ® which is a skin-care lotion contained in tiny egglike globes that are popped and rubbed onto the face. A problem with round packaging lies in the tendency for them to roll away. There is also no easy handle by which they may be gripped.

As an answer to the roll-away problem, U.S. Pat. No. 5,063,057 (Spellman et al) discloses a cosmetic capsule having a round body with hollow chamber forming a major portion of the capsule, a tab forming a minor portion of the capsule and a neck section connecting the tab with the round body. Upon twisting, the neck can be broken to allow release of the cosmetic composition from within the chamber. Circumferentially encompassing the round body is an outwardly projecting ring functioning to prevent undesirable roll. Although the patent may have solved the roll problem, there still remains the difficulty of consumers being unable to adequately grip the article. Considerable torque is necessary for twist-off of the tab. A solid grip is, therefore, essential to render the article convenient in use.

Accordingly, it is an object of the present invention to provide a cosmetic product delivered in a capsule which avoids many of the problems associated with the known art.

A more specific object of the present invention is to provide a cosmetic composition contained within a capsule whose seal can readily be broken without the aid of a piercing instrument.

A further object of the present invention is to provide a cosmetic composition contained within a capsule whose shape is distinctly different from that of typical vitamin capsules.

A still further object of the present invention is to provide a cosmetic composition contained within a capsule that is spheroidal yet has means for preventing undesirable roll and has means for being gripped by the fingers.

Other objects, features and advantages of this invention will become more apparent upon reference to the following detailed description and drawings illustrating a preferred embodiment thereof.

SUMMARY OF THE INVENTION

A cosmetic product is provided comprising:

a cosmetic composition pharmaceutically acceptable for application to a human body; and a capsule completely enclosing the cosmetic composition, the capsule comprising:

(i) a spheroidal body defined by an outer wall and having a hollow chamber, the spheroidal body forming a major portion of the capsule, the spheroidal body also including at least two wings on opposite sides of the spheroidal body perpendicularly extending outward therefrom;

(ii) a tab forming a minor portion of the capsule; and (iii) a neck section connecting the tab with the spheroidal body, the neck section upon being twisted breaking to allow exit of the composition from the chamber.

The plurality of wings advantageously are formed unitarily with the spheroidal body. Each wing preferably has a flat upper and lower surface and an outer edge whose contour is different than the contour of the spheroidal body. Advantageously, the outer edge contour includes both a concave and convex profile. Furthermore, an end of the wing distant from the tab will be in the form of a wedge having a point directed away from both the tab and the spheroidal body. Preferably, the wing will have a width of variable length as measured by a distance between the outer wall of the spheroidal body and the edge of the wing.

A variety of substances may be employed to form walls of the capsule. Most preferred as the wall-forming substance is gelatin. Since gelatin is water-soluble, it is important with this embodiment to ensure that the cosmetic product is relatively anhydrous. Among suitable cosmetic compositions are those in lotion, cream or paste form. These products are intended for application to either hair or skin. The skin compositions may include agents providing sunscreen, tanning, antiwrinkling, antidandruff, antiacne, moisturizing and hair growth benefits.

BRIEF DESCRIPTION OF THE DRAWING

The accompanying drawing will more fully illustrate selected embodiments of the present invention wherein.

DETAILED DESCRIPTION

FIGS. 1-5 illustrate a preferred embodiment of the present invention. The capsule includes a major portion which is a spheroidal body having a hollow chamber 2 containing a cosmetic composition pharmaceutically acceptable for application to skin or hair. In the preferred embodiment the spheroidal body is an oblate spheroid; however, other spheroidal shapes such as round are also within the concept of this invention. A tab 4 forms a minor portion of the capsule. This tab preferably may be either round or oblong in shape. To connect tab 4 with the chamber 2, there is provided a neck section 6 which is hollow along at least a partial length thereof.

Figure 1:
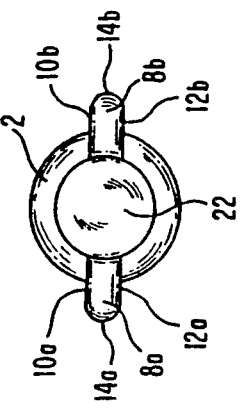
FIG. 1 is a perspective elevational view showing the capsule.
Figure 2:
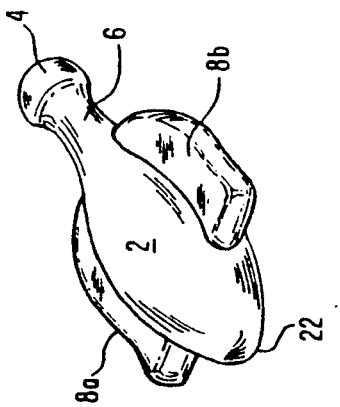
FIG. 2 is a side elevational view of the capsule according to FIG. 1.
Figure 3:
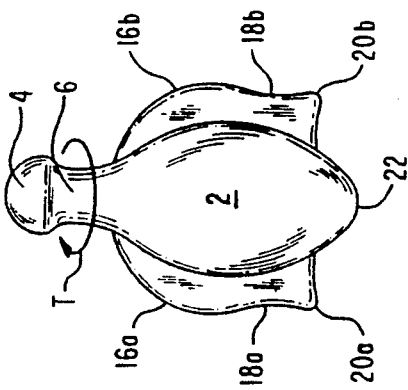
FIG. 3 is a front plan view of the capsule according to FIG. 1.
Figure 4:
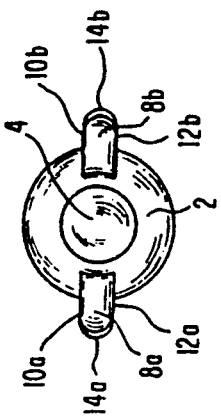
FIG. 4 is a bottom view of the capsule according to FIG. 1.
Figure 5:
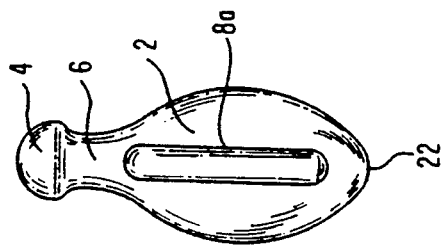
FIG. 5 is a top view of the capsule according to FIG. 1.

On opposite sides of the spheroidal body are wings 8a, 8b which perpendicularly extend outward from the spheroidal body. Each of wings 8a, 8b have, as best shown in FIGS. 4-5, a flat upper surface 10a, 10b and a parallel lower surface 12a, 12b. Between the upper and lower surfaces of each wing is an edge surface 14a, 14b outermost from the spheroidal body 2. Wings 8a, 8b are contoured such that edge surfaces 14a, 14b describe a concave 16a, 16b and convex 18a, 18b profile. At an end of the wings 8a, 8b distant from 4, the upper, lower and edge surfaces form a wedge 20a, 20b that points away from tab 4 and from a bottom end 22 of spheroidal body 2.

Tab 4 can serve as a gripping handle but most important, provides a twist-off opening mechanism. The capsule is easily punctured by twisting tab 4 in the direction T until the neck section 6 snaps thereby causing an opening into the chamber. See FIG. 3. By gentle squeezing of the capsule walls, cosmetic composition is forced to exit through the puncture opening.

Any cosmetic composition may be employed provided it is pharmaceutically acceptable for application to the human skin or hair. There is the further proviso that the cosmetic composition must also be compatible with the substance that comprises the walls of the capsule.

Capsules of the present invention may be formed from a wide variety of substances which may be of natural or synthetic origin. Most preferred for the present invention is the natural substance commonly known as gelatin.

Gelatin walls may either be soft or hard. Preferably, however, the walls are elastic or soft. Gelatin for soft capsules normally will be selected from low-bloom Type A (170-180 g), Type B (150-172 g), or a mixture of Types A and B. The manufacturing process for preparing such capsules can utilize a rotary die fed from two plasticized gelatin sheets which form a sealed chamber or compartment around the material being encapsulated. The size of the capsules may range from No. 0 to 2. Diameter of the combined ring and body may range from about 0.5 to about 5 cm, preferably about 1 to about 3 cm, optimally about 1.5 cm. Tab and neck combination will normally be shorter in length than the combined ring and body diameter and will range from about 0.1 to about 2 cm, preferably about 0.3 to about 1 cm. Amounts of cosmetic product held within these capsules may range in weight anywhere from about 0.05 to about 5 grams, preferably from about 0.3 to about 2 grams, optimally about 1 gram.

A large variety of synthetic polymers may be utilized as the wall-forming substance. The polymers may either be water-soluble or water-insoluble. Suitable materials are polymers derived from such monomers as vinyl chloride, vinyl alcohol, vinyl pyrrolidone, furan, acrylonitrile, vinyl acetate, methyl acrylate, methyl methacrylate, styrene, vinyl ethyl ether, vinyl propyl ether, acrylamide, ethylene, propylene, acrylic acid, methacrylic acid, maleic anhydride, salts of any of the aforementioned acids and mixtures thereof. These materials may be in the form of either homo or copolymers. More specific examples include polyvinyl chloride, polypropylene, acrylic/maleic copolymers, sodium polyacrylate, polyvinyl pyrrolidone and polyvinyl alcohol.

Cellulose based materials may also be suitable; these include sodium carboxymethyl cellulose, hydroxypropyl methyl cellulose, ethyl cellulose, cellulose acetate and cellulose sulphate esters.

Injection molding and extrusion processes are preferable handling procedures when employing synthetic polymers for the present invention. It is also to be understood that plasticizers, protective coatings and other functional additives may be incorporated within the wall material.

Lotion, cream and paste forms may be packaged within the capsule. These compositions may either be anhydrous, aqueous or in emulsion form, the latter encompassing both oil-in-water and water-in-oil emulsions.

Cosmetic compositions of the present invention generally will contain a vehicle or a carrier which is inert, usually an ingredient present in highest amounts, and functioning to deliver active or performance ingredients. The amount of vehicle may range from about 5 to about 99%, preferably from about 25 to about 80% by weight of the total composition.

Where the capsule wall material is water sensitive, such as where gelatin, polyvinyl alcohol or polyvinyl pyrrolidone are employed, a nonaqueous carrier becomes necessary. Especially useful in this situation is a silicone polymer, preferably a polydimethyl siloxane and/or a polydimethyl phenyl siloxane. Silicones of this invention may be those with viscosities ranging anywhere from about 10 to 10,000,000 centistokes at 25° C. Especially desirable are mixtures of low and high viscosity silicones. These silicones are available from the General Electric Company under the trademarks Vicasil, SE and SF and from the Dow Corning Company under the 200 and 550 Series. Amounts of silicone which can be utilized in the compositions of this invention range anywhere from 5 to 95%, preferably from 25 to 90% by weight of the composition.

Surfactants, which are also sometimes designated as emulsifiers, may be incorporated into the cosmetic compositions of the present invention. Surfactants can comprise anywhere from about 0.5 to about 30%, preferably from about 1 to about 15% by weight of the total composition. Surfactants may be cationic, nonionic, anionic, or amphoteric in nature and combinations thereof may be employed.

Illustrative of the nonionic surfactants are alkoxylated compounds based upon fatty alcohols, fatty acids and sorbitan. These materials are available, for instance, from the Shell Chemical Company under the "Neodol" designation. Copolymers of polyoxypropylene-polyoxyethylene, available under the Pluronic trademark sold by the BASF Corporation, are sometimes also useful. Alkyl polyglycosides available from the Henkel Corporation similarly can be utilized for the purposes of this invention.

Anionic-type surfactants may include fatty acid soaps, sodium lauryl sulphate, sodium lauryl ether sulphate, alkyl benzene sulphonate, mono and dialkyl acid phosphates and sodium fatty acyl isethionate.

Amphoteric surfactants include such materials as dialkylamine oxide and various types of betaines (such as cocoamido propyl betaine).

Emollients are often incorporated into cosmetic compositions of the present invention. Levels of such emollients may range from about 0.5 to about 50%, preferably between about 5 and 30% by weight of the total composition. Emollients may be classified under such general chemical categories as esters, fatty acids and alcohols, polyols and hydrocarbons.

Esters may be mono- or diesters. Acceptable examples of fatty diesters include dibutyl adipate, diethyl sebacate, diisopropyl dimerate, and dioctyl succinate. Acceptable branched chain fatty esters include 2-ethylhexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl erucate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5 to 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Various types of active ingredients may be present in cosmetic compositions of the present invention. Actives are defined as skin or hair benefit agents other than emollients and other than ingredients that merely improve the physical characteristics of the composition. Although not limited to this category, general examples include sunscreens, tanning agents, skin antiwrinkling agents, antidandruff agents, antiacne agents and hair growth stimulants.

Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Antiwrinkling agents are best exemplified by the 2-hydroxyalkanoic acids, prostaglandins, retinoic acids, ceramides and their derivatives. These agents may be present anywhere from about 0.00001 to about 5%, preferably from about 0.0001 to about 1%, optimally between about 0.01 and 0.2% by weight of the total composition. Most preferred of the active compounds mentioned above is 2-hydroxyoctanoic acid, lactic acid, retinol and pigskin or bovine-brain lipid ceramides as well as salts of active compounds. Further identification of ceramide structures may be found in U.S. Pat. No. 4,950,688 (Bowser et al), herein incorporated by reference.

Vitamins may also be included in the compositions of the present invention. Especially preferred is vitamin A palmitate (retinyl palmitate) and vitamin E linoleate (tocopheryl linoleate). Other esters of vitamins A and E may also be utilized.

Many cosmetic compositions, especially those containing water, must be protected against the growth of potentially harmful microorganisms. Preservatives are, therefore, necessary. Suitable preservatives include alkyl esters of p-hydroxybenzoic acid, hydantoin derivatives, propionate salts, and a variety of quaternary ammonium compounds.

Particularly preferred preservatives of this invention are methyl paraben, propyl paraben, imidazolidinyl urea, sodium dehydroxyacetate and benzyl alcohol. Preservatives will usually be employed in amounts ranging from about 0.5% to 2% by weight of the composition.

Powders may be incorporated into the cosmetic compositions of the invention. These powders include chalk, talc, Fullers earth, kaolin, starch, smectites clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these materials may range anywhere from 0.001 up to 20% by weight of the composition.

The following examples will more fully illustrate selected embodiments of this invention. All parts, percentages and proportions referred to herein and in the appended claims are by weight unless otherwise indicated.

EXAMPLE 1

A gelatin capsule is prepared having a structure as depicted in the drawing and containing the following cosmetic composition:

TABLE I

| Skincare Treatment | |
|---|---|
| Ingredient | Weight % |
| Silicone Fluid 344 | 57.940 |
| Silicone Fluid 345 | 20.000 |
| Silicone Gum SE-30 | 10.000 |
| Squalene | 9.500 |

TABLE I-continued

| Skincare Treatment | |
|---|---|
| Ingredient | Weight % |
| C12–C15 Fatty Alcohol Benzoate | 1.000 |
| Vitamin E Acetate | 1.000 |
| Ceramax (a mixture of phospholipids, lecithin and Ceramide II) | 0.010 |
| α-Hydroxyoctanoic Acid | 0.050 |
| Vitamin A Palmitate | 0.500 |
| Ceramide II (N-palmitoyl-2-aminohexadecan-1,3-diol) | 0.001 |

EXAMPLE 2

A polyacrylamide capsule is prepared having a structure as depicted in the drawing and containing the following cosmetic composition:

TABLE II

| Suntan Lotion | |
|---|---|
| Ingredient | Weight % |
| Water | 86.00 |
| ACETULAN ® (cetyl acetate and acetylated lanolin alcohol) | 4.00 |
| Propylene glycol | 3.00 |
| Stearic acid | 2.00 |
| Dow Corning 556 Fluid (phenyl dimethicone) | 1.00 |
| VEEGUM ® (modified magnesium aluminum silicate) | 1.00 |
| Cetyl alcohol | 0.50 |
| Triethanolamine | 0.50 |
| Octyl methoxycinnamate | 1.00 |
| Oxybenzone | 1.00 |
| Preservatives | QS |

EXAMPLE 3

A cellulose acetate capsule is prepared having a structure as depicted in the drawing and containing the following composition:

TABLE III

| Acne Lotion | |
|---|---|
| Ingredient | Weight % |
| Deionized water | 82.60 |
| Glycerin | 3.00 |
| Glyceryl monstearate | 3.00 |
| Smectite clay | 2.00 |
| Stearyl alcohol | 1.00 |
| Isocetyl stearate | 1.00 |
| Preservatives | 0.40 |
| Benzoyl peroxide | 7.00 |

EXAMPLE 4

A polypropylene capsule is prepared having a structure as depicted in the drawing and containing the following cosmetic composition:

TABLE IV

| Skin Wrinkle Smoother | |
|---|---|
| Ingredients | Weight % |
| Water | 82.50 |
| FLEXAN 130 ® (sodiium polystyrene sulfonate) | 12.00 |
| Collasol soluble collagen | 3.00 |
| Modified magnesium aluminum silicate | 1.50 |
| Cellulose gum CMC-7LF | 1.00 |

EXAMPLE 5

A polyvinyl alcohol capsule is prepared having a structure as depicted in the drawing and containing the following cosmetic composition:

TABLE V

| Antidandruff Shampoo | |
|---|---|
| Ingredient | Weight % |
| Water | 58.55 |
| TEA lauryl sulfate (40%) | 25.00 |
| Hamposyl L-30 fatty acid sarcosinate | 10.00 |
| Zinc pyrithione (48%) | 4.20 |
| Hydroxypropyl methylcellulose | 1.25 |
| Modified magnesium aluminum silicate | 1.00 |

EXAMPLE 6

A polyvinyl pyrrolidone capsule is prepared having a structure as depicted in the drawing and containing the following cosmetic composition:

TABLE VI

| Hair Growth Stimulant | |
|---|---|
| Ingredient | Weight % |
| Water | 60.15 |
| Sodium lauryl ether sulfate | 28.00 |
| Sodium sulfate | 10.00 |
| Lanolin alcohol | 1.00 |
| Polyoxyethylene 20 sorbitan | 0.50 |
| MINOXIDIL ® ((6-)1-piperidinyl-2,4-pyrimidinediamine 3-oxide) | 0.25 |
| Methylparaben | 0.10 |

The foregoing description and examples illustrate selected embodiments of the present invention and in light thereof variations and modifications will be suggested to one skilled in the art, all of which are within the spirit and purview of this invention.

What is claimed is:

1. A cosmetic product comprising:
   a cosmetic composition pharmaceutically acceptable for application to a human body; and
   a capsule completely enclosing the cosmetic composition, the capsule comprising:
   (i) a spheroidal body defined by an outer wall and having a hollow chamber, the spheroidal body forming a major portion of the capsule, the spheroidal body also including at least two wings on opposite sides of the spheroidal body perpendicularly extending outward therefrom;
   (ii) a tab forming a minor portion of the capsule; and
   (iii) a neck section connecting the tab with the spheroidal body, the neck section upon being twisted breaking to allow exit of the composition from the chamber, and said spheroidal body at an end thereof opposite that of said tab being fee of any wing projecting outward therefrom.

2. A product according to claim 1 wherein said hollow chamber has a capacity for holding from about 0.05 to about 5 grams of said cosmetic composition.

3. A product according to claim 1 wherein at least a portion of said neck section is hollow.

4. A product according to claim 1 wherein said capsule has walls formed from a gelatin.

5. A product according to claim 1 wherein said capsule has walls formed of homo and copolymers derived from polymerization of a monomer selected from the group consisting of vinyl chloride, vinyl alcohol, vinyl pyrrolidone, furan, acrylonitrile, vinyl acetate, methyl acrylate, methyl methacrylate, styrene, vinyl ethyl ether, vinyl propyl ether, acrylamide, ethylene, propylene, acrylic acid, methacrylic acid, maleic anhydride, salts of any of the aforementioned acids and mixtures thereof.

6. A product according to claim 5 wherein said substance forming said capsule is polyvinyl alcohol.

7. A product according to claim 1 wherein said cosmetic composition comprises a vehicle selected from the group consisting of water, silicone polymer and mixtures thereof.

8. A product according to claim 1 wherein said cosmetic composition is anhydrous.

9. A product according to claim 8 wherein said cosmetic composition includes a silicone polymer as a major component thereof.

10. A product according to claim 1 wherein said cosmetic composition comprises an active ingredient selected from the group consisting of sunscreens, suntanning agents, skin antiwrinkling agents, antidandruff agents, antiacne agents, hair growth stimulants and mixtures thereof.

11. A product according to claim 1 wherein said at least two wings are in a common plane equatorially cutting said spheroidal body and said plane also intersects with said tab.

12. A product according to claim 1 wherein an outward edge of said wings possesses a concave and convex profile.

13. A product according to claim 1 wherein said wings at an end thereof distant from said tab form a wedge pointing away from said spheroidal body.

* * * * *